United States Patent [19]

Caldwell et al.

[11] Patent Number: 4,935,009

[45] Date of Patent: Jun. 19, 1990

[54] EMERGENCY DRUG INJECTION SYSTEM

[76] Inventors: James B. Caldwell, 48 Madison Pl., Annapolis, Md. 21401; Paul J. Vitale, 651 Kensington Ave., Severna Park, Md. 21146

[21] Appl. No.: 205,067

[22] Filed: Jun. 10, 1988

[51] Int. Cl.$^5$ .............................................. H61M 5/14
[52] U.S. Cl. ........................................ 604/56; 604/83; 604/218
[58] Field of Search ...................... 604/82, 83, 80, 36, 604/38, 218, 56, 256

[56] References Cited

U.S. PATENT DOCUMENTS

| | | |
|---|---|---|
| 2,825,334 | 8/1953 | Das, Sr. . |
| 2,854,027 | 12/1956 | Kaiser et al. . |
| 2,866,457 | 12/1956 | Moore . |
| 4,005,710 | 2/1977 | Zeddies et al. . |
| 4,051,852 | 10/1977 | Villari . |
| 4,114,617 | 9/1978 | Turner et al. . |
| 4,244,366 | 1/1981 | Raines . |
| 4,246,932 | 1/1981 | Raines . |
| 4,335,717 | 6/1982 | Bujan .................................... 604/83 |
| 4,411,661 | 10/1983 | Kersten . |
| 4,504,265 | 3/1985 | Rudzena et al. . |
| 4,585,435 | 4/1986 | Vaillancourt . |

OTHER PUBLICATIONS

Closed-Chest Cardiac Massage, Dr. James Caldwell, Jul. 9, 1960, pp. 1064-1067.
"Therapy Reviews", Advances in Drug Therapy of Cardiopulmonary Arrest, Cynthia L. Raehl, Feb. 1987, 118-139.
Part III: Adult Advanced Cardiac Life Support, Jama, Jun. 6, 2993-2953.
Differences in Drug Delivery with Peripheral and Central Veno Injections: Normal Perfusion, William G. Barsan, MD et al., May 9, 1985, pp. 1-3.
Peripheral Versus Central Venous Delivery of Medications During CPR, Lynnette A. Doan, Sep. 1984, pp. 784/37-786/39.
Lidocaine Levels During CPR: Differences After Peripheral Venous, Central Venous, and Intracardiac Injections, William G. Barsan et al., Feb. 1981, pp. 73/9-78/14.
Peripheral VS Central Circulation Times During CPR: A Pilot Study, Gloria J. Kuhn et al., Aug. 1981, pp. 28/417-30/419.
Central Versus Peripheral Intravenous Routes in Cardiopulmonary Resuscitation, Jerris R. Hedges et al., May 1983, pp. 385-390.
"Annuals of Emergency Medicine" Effect of Peripheral Versus Central Injection of Epinephrine on Changes in Aortic Diastol Pressure During Closedchest Massage in Dogs, S. Keats et al., May 1985, p. 495.
"Annans of Emergency Medicine" Comparison of Epinphrine and Phenylephrine for Resuscitation and Neurologic Outcome of Cardiac Arrest in Animals, J. C. Brillman et al.; May 1985, p. 495.
"Annals of Emergency Medicine" Value of Epinephrine in Prehospital CPR, J. S. Stapczynski et al., May 1985, p. 495.
Principles and Practice of Emergency Medicine, Schwartz, 1986, p. 255.

Primary Examiner—Stephen C. Pellegrino
Attorney, Agent, or Firm—Foley & Lardner, Schwartz, Jeffery, Schwaab, Mack, Blumenthal & Evans

[57] ABSTRACT

A method and apparatus for forcefully injecting drugs into circulatory decompensated patients uses a flush solution to push a peripheral injection of a standard drug dose into central circulation. A pump in a single unit allows rapid repeated flushes and allows one person to administer the drug and flush solution simultaneously. Separate drug and flush administration means reduced potential confusion about whether a drug was administered.

21 Claims, 8 Drawing Sheets

EMERGENCY DRUG INJECTION SYSTEM

BACKGROUND OF THE INVENTION

1. Field Of The Invention

The invention is an Emergency Drug Injection and Circulatory Distribution Control Device (EDICDD) which can be used to administer drugs forcefully into circulatory decompensated human or animal patients.

2. Background Art

CPR is a general term that encompasses both basic life support (BLS), consisting of manual chest compression and ventilation, and advanced cardiac life support (ACLS), involving the more sophisticated techniques and technology utilized in CPR. Included within the domain of ACLS is drug therapy and considerations in drug administration.

Until recently, drug therapy standards for ACLS had developed empirically, with little supporting scientific data, despite their critical roles in resuscitation. Within the past several years, data has been obtained from both animal and clinical studies which challenge the adequacy of the traditional drug protocols, including those involving the routes of drug administration during cardiac arrest. See, Barsan, Hedges, Nishiyama and Lukes, Differences in Drug Delivery With Peripheral and Central Venous Injection. *American Journal of Emergency Medicine.* Vol. 4, No. 1, p.1, January 1986, hereinafter, Barsan, Hedges et al; Doan, Peripheral versus Central Venous Delivery of Medications during CPR, *Annals of Emergency Medicine (Part 2)* 13:784786, September 1984, hereinafter, Doan; Barsan, Levy and Weir, Lidocaine Levels During CPR: Differences After Peripheral Venous, Central Venous and Intracardiac Injections, *Annals of Emergency Medicine* 10:73-78, February 1981, hereinafter, Barsan, Levy, et al; Kuhn, White, Swetnam, Mumey, Rydesky, Tintinalli, Krome, and Hoehner, Peripheral versus Central Circulation Times During CPR: A Pilot Study, *Annals of Emergency Medicine* 10:417-419 August 1981, hereinafter Kuhn, et al; Hedges, Barsan, Doan, Joyce, Lukes, Dalsey and Nishiyama, Central Versus Peripheral Intravenous Routes in Cardiopulmonary Resuscitation, *American Journal of Emergency Medicine*, Vol. 2, No. 5, Page 385, September 1984, hereinafter, Hedges, et al; Keats, Jackson, Kosnick, Tworek and Zawanger, Effect of Peripheral Versus Central Injection of Epinephrine or Changes in Aortic Diastolic Pressure During Closed Chest Massage in Dogs, *Annals of Emergency Medicine* 14:495, May 1985, hereinafter. Keats et al.

In 1985, The National Conference on Standards and Guidelines for Cardiopulmonary Resuscitation (CPR) and Emergency Cardiac Care (ECC), sponsored by the American Heart Association, examined treatment guidelines for CPR that had been established by previous conferences. In light of scientific and clinical data available since 1979, the 1985 Conference substantially revised these guidelines, particularly in the areas of drug therapy and methods of administration. In 1986, all of the revised standards and guidelines from this conference were published in the Journal of the American Medical Association and have become the basis for current medical practice during ACLS. See, Standards for CPR & ECC Part III: Adult Cardiac Life Support, *Journal of American Medical Assn.*, Vol 225, No. 21, Page 2933, June 6, 1986, hereinafter, Standards.

An essential component of ACLS is the early establishment of a reliable intravenous line for the administration of drugs and fluids. The 1985 Conference drew three important conclusions relative to this that have also been embraced by the American Heart Association:

1. Avoid intra-cardiac injection.
2. When available, always use a central venous catheter to inject drugs.
3. CPR is not to be interrupted for the insertion of a central venous catheter, therefore drugs may be administered via peripheral intravenous sites. In these instances, the drug injection is to be followed by the injection of a flush solution to facilitate drug entrance into the general circulation.

While current scientific data show that a central venous catheter is the superior route for drug administration during CPR, See, Kowenhoven, W. B., Jude, J. R., Knickerbocker, C. G., Closed-chest Cardiac Massage, *JAMA* 1960:173:1064-7; Raehl, Advances in Drug Therapy of Cardiopulmonary Arrest, *Clinical Pharmacy*, Vol. 6, February 1987, p. 118, hereinafter, Raehl; American Heart Associaton and National Academy of Sciences National Research Council: Standards and Guidelines For Cardiopulmonary Resusciation (CPR) and Emergency Cardiac Care (ECC), *JAMA* 1986: 255:2905-92; Barsan, Hedges, et al; Doan; Barsan, Levy, et al; Kuhn, et al; Hedges, et al; Keats, et al, in actuality, this route is frequently not possible, particularly in the non-institutional setting. Attempts at cannulating patients for central venous catheterization during CPR are not recommended due to the increase risk of inducing pneumothorax when the patient is being bounced by cardiac compressions. See, Schwartz, *Principes & Practice of Emergency Medicine,* 1986, hereinafter, Schwartz. Furthermore, such measures may require interruption of CPR at a stage when priority must be given to ventilation, oxygenation and chest compression. Therefore, if no central vein has been cannulated prior to the arrest, cannulation of the peripheral antecubital vein should be the site of first choice. Id.

Advantages of peripheral venous cannulation are that is easier, quicker, results in fewer complications, and does not require interruption of CPR. Since the majority of affected patients will initially require drug therapy using a peripheral vein, a method for achieving rapid and high blood concentrations of drug using the peripheral route has been outlined in the "Standards of CPR and ECC". The guidelines recommend using a large volume of flush solution following the injection of a drug in order to more rapidly distribute the drug into the central circulation. See, Standards. This system is considered equivalent to using a central venous catheter for drug administration. Unfortunately, this system also poses some problems in terms of safety and practicality. The flush solution (30–60 milliliters) needs to be injected immediately following drug administration. This requires that the flush solution be administered by a syringe that has been prepared just prior to administration, a labor and time intensive task. In addition, each time the flush solution is given, the closed sterile system needs to be entered (broken). These steps must be repeated numerous times during a cardiac arrest since a multiplicity of drugs are injected as frequently as every few minutes for as long as 20 to 40 minutes. With these points in mind, the disadvantages inherent to such an arrangement are as follows:

1. Critical time is lost since each new flush requires preparation and in insertion of an additional syringe.

2. The quantity of contaminated "dirty" needles created will raise the risks to health care providers of infectious disease exposure.

3. It will require an extra person in an already crowded situation to prepare flush solutions.

4. Confusion may occur as to whether or not a drug has been given since both drug and flush are colorless liquids.

5. The chance of introducing air embolus or bacteria (and subsequent infection) is increased each time the sterile system is broken for the extra flush solution.

6. The supplies needed, and thus cost and storage space for emergency cart supplies, are increased.

At the present there are no devices currently available designed to administer drugs forcefully into circulatory decompensated patients for example, during cardiopulmonary arrest. The Emergency Drug Injection and Circulatory Distribution Device (EDICDD) disclosed is designed to carry out this function. Although, many of the parts of the EDICDD are derived from already existing commercially available products, none of these products are designed to perform the vital functions of the EDICDD.

U.S. Pat. No. 2,866,456 (Moore) demonstrates a means of administering parenteral fluids into an intravenous tubing set-up. This device does not concern itself with drawing fluid from a reservoir aseptically or forcefully injecting drugs into circulation. U.S. Pat. No. 4,114,617 (Turner) is also designed to administer supplemental drugs (blood) into an already existing operational intravenous system. Turner used check valves, but these are of common nature and are found in other devices. Once again Turner's apparatus does not provide a mechanism by which drugs can be forcefully injected into a patient's circulation. Villari, U.S. Pat. No. 4,051,852 contains one-way check valves similar to those described in the EDICDD, but once again these are of common type and design, and this device by Villari is not intended to forcefully administer drugs into a patient's general circulation.

Kas, U.S. Pat. No. 2,825,334, deals with a check valve system similar to that used in the EDICDD, which are common devices utilized routinely. The recoil mechanism of Kas is similar to that of the EDICDD, but does not contain guiding rods, and is not designed maintain sterility after multiple injections (the plunger shaft). This device was designed to be used for livestock only.

The spike apparatus described in Kersten, U.S. Pat. No. 4,411,661, is similar to that of the EDICDD and is a common component of intravenous tubings found with many brands of tubings. This device is designed to allow fluid to flow from a fluid reservoir into intravenous tubing maintaining a closed system and sterility.

Kaiser, et al, U.S. Pat. No. 2,854,027, deals With a valve system providing similar actions as the EDICDD valve apparatus part 15, however, the mechanics of these two systems are different and not comparable. The art of Zeddies, et al., U.S. Pat. No. 4,005,710, deals with an injection port similar to the injection port numbered 55 of the EDICDD. Once again this injection port is a common device utilized on many types of intravenous tubing sets This injection port, with its one-way valve, allows for a drug to be injected into an intravenous tubing set while preventing a backflow of fluid/drug in the tubing, by way of the one-way valve. The device by Rudenza et al, U.S. Pat. No. 4,504,265, primarily concerns administering a bolus of medication quickly when upstream flow of an intravenous fluid is slow and may delay delivery of the medication. It is of a controlled rate and not designed to deliver medications during cardiopulmonary arrest and circulatory collapse in critical situations. The piston/syringe mechanism of Rudenza et al does not involve one-way valves, and the syringe with fluid needs to be inserted into the piston with each injection. Villancort, U.S. Pat. No. 4,585,435 deals with an extension set designed to allow administration of two different drugs/fluids simultaneously. This device does not contain valves or a syringe/plunger apparatus for rapid delivery of drugs into a patient's circulation under critical conditions.

Two patents by Raines, U.S. Pat. No. 4,244,366 and No. 4,246,932 deal with a syringe stroke controlling device and a multiple additive valve assembly, respectively. These two devices are used together in an apparatus for aspirating fluid from a container into a calibrated syringe. Adjustable guiding pins are utilized in order to control the volume of fluid in the syringe. The syringe used is 10 ml. in volume and, if used repeatedly for many aspirations and pumping, must be contained in a sterile environment in order to maintain its sterility. The EDICDD contains a 60 ml syringe with a nonadjustable internal volume of 25 ml designed to help maintain sterility after multiple injections and recoil. The recoil mechanisms of Raines and the EDICDD are similar. However, that of the EDICDD is designed for a 25 ml. volume and is covered to enable maintaining sterility during use in an open environment. This covered plunger shaft/recoil mechanism protects the EDICDD from spilled blood, fluids, and user touch contamination. The EDICDD, in addition, contains tubing and an injection port for the administration of other drugs/fluids. The valves on the EDICDD need not be specifically similar to those of Raines, but can be of any type of construction.

SUMMARY OF THE INVENTION

In view of the foregoing it is an object of the invention to pump flush solution needed to "push" the peripheral injection of a standard drug dose during procedures such as CPR into the central circulation to enable a drug to reach the vital organs to exert its effects, without the disadvantages of currently used methods.

It is a further objective of the invention to save critical time by providing rapid repeat flushes.

It is a further objective of the invention to provide a pump in a single unit to minimize cost and storage of supplies.

It is a further objective of the invention to eliminate the need for additional needles.

It is a further objective of the invention to provide separate and different drug and flush administration means thereby reducing potential confusion over whether a drug was administered.

It is a further objective of the invention to reduce the likelihood of additional breaks in the sterile system, thereby reducing risks of infection or fatal embolism.

It is a further object of the invention to facilitate administration of both a drug and a flush solution by a single person.

An advantage of the invention is that it provides a most effective means of administering drugs peripherally during CPR. By safely and rapidly pushing drugs into the circulatory system, the invention can make peripheral drug therapy truly comparable to using a central venous catheter, improving outcomes and saving lives in cardiopulmonary arrest victims.

BRIEF DESCRIPTION OF THE DRAWINGS

The invention will now be described by way of example and with reference to the accompanying drawings in which.

DETAILED DESCRIPTION OF THE PREFERRED EMBODIMENTS

Figure 1:
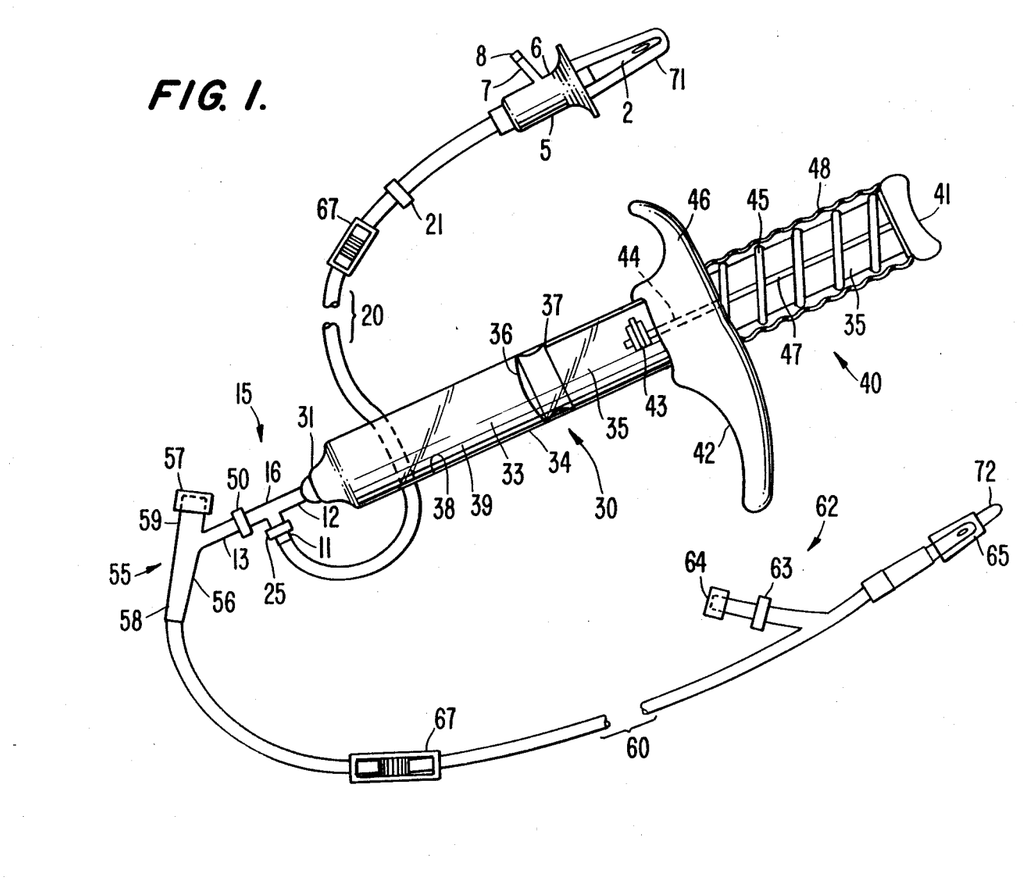
FIG. 1 is a perspective showing the emergency drug injection and circulatory distribution device embodying the teachings of the present invention.
Figure 6:
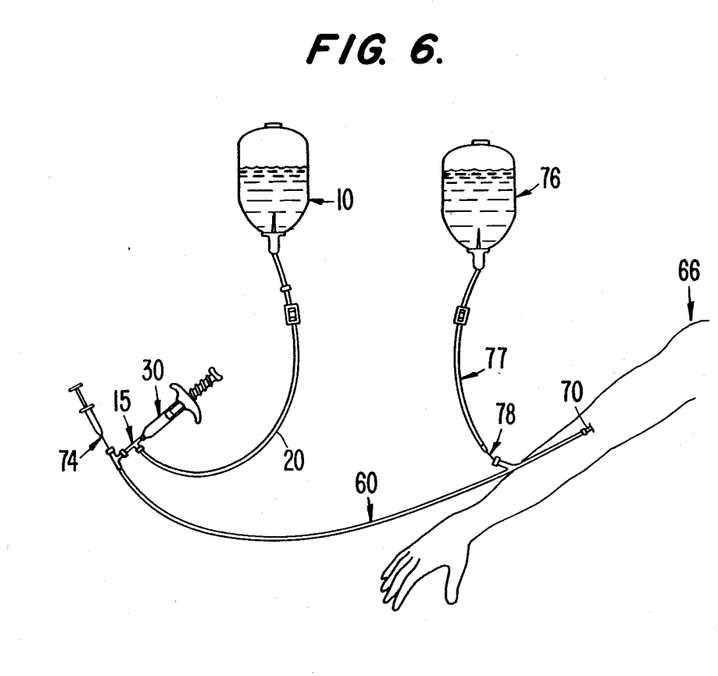
FIG. 6 is an illustration of the present invention as it would be attached to the fluid reservoir, a maintenance intravenous fluid and to a patient.

Referring to FIG. 1, there is shown a device embodying the present invention which is generally designed for the rapid administration and vascular circulatory distribution of emergency intravenous drugs. This device includes a reservoir spike 5 for connection to a parenteral fluid reservoir container 10. The spike 5 is permanently attached to a length of flexible conduit or tubing 20, hereinafter known as the upstream tubing, which contains a hydrophilic filter 21 and fluidly connects the spike 5 with the valve apparatus 15. The valve apparatus also connects to a pump means 30, generally a syringe, having an automatic recoil mechanism 40 and to a second length of flexible tubing or conduit 60, hereinafter know as the downstream tubing. The downstream tubing 60 contains: an injection port 55 adjacent to the valve apparatus; a Y-site 62 with a one-way check valve 63 near its terminal end; a male luer lock connector 65 for attachment to a standard intravenous needle or catheter 70, as illustrated in FIG. 6. The term "connected", as used in the present specifications and the appended claims, meaning either a direct connection or connection through a conduit. The term "reservoir fluid" shall likewise means parenteral fluid which is drawn into the invention from the parenteral fluid reservoir container 10.

The reservoir spike 5 is of conventional design and construction such as is known to those familiar with the art. It generally consists of a piercing hollow leg 2 for the purpose of penetrating a puncturable stopper on a standard parenteral fluid container 10, an easily gripable body 6, and an air vent 7 containing a suitable 0.22 micron bacterial filter 8. Said filter is used for the occasion when the invention is used with a non-collapsible and non-vented fluid container 10. The hollow leg 2 communicates, through a bore in the body 6, with the upstream tubing 20 to which it is permanently attached.

The upstream tubing 20 is of a length appropriate to allow operationally comfortable connection between the fluid reservoir 10 and the valve apparatus 15. A hydrophilic filter 21 is located at a short distance, along the upstream tubing 20, from the reservoir spike 5. The purpose of the hydrophilic filter 21 is to "lock" the system, preventing passage of air through the filter if, after priming, air from an empty reservoir 10 should enter the upstream tubing 20. This will serve to prevent entry of air into the valve and syringe mechanisms, thus preventing inadvertent injection of air bolus into a patient. The downstream terminal of the upstream tubing 20, is permanently secured to the valve apparatus 15 at the valve supply inlet port 11.

The valve apparatus 15 consists of two one-way fluid check valves 25, 50 fluidly connecting each other, the valve supply port 11, the valve-to-syringe connector 12, and the valve-to-tubing outlet port 13 as described in detail below. Alternatively, the valves may be included as the multiple additive valve assembly described in U.S. Pat. No. 4,246,932.

The valve apparatus 15 will generally be constructed of a clear rigid material. The valve supply port 11 is permanently connected to the upstream tubing 20 and to the inlet check valve 25 at the opposite end. The inlet check valve 25 is a one-way fluid valve which is oriented to permit free fluid flow from the valve supply port 11 into the valve-to-syringe connector 12 or outlet check valve 50 while preventing fluid flow in the opposite direction.

The inlet check valve 25 is permanently connected to the valve apparatus body 16, which is in the form of a "T" shaped passageway serving fluidly connect the valve-to-syringe connector 12 to both of the one-way fluid check valves 25 and 50 within the valve apparatus 15. The valve-to-syringe connector 12 is designed with an inner bore adequate to accept the nozzle 31 of the pump means 30 in a sealed fashion. This connection will be made nondetachable in order to prevent separation of the pump means 30 from the valve apparatus 15 during operation.

The outlet check valve 50 is connected in-line between the valve apparatus body 16 and the valve-to-tubing outlet port 13. The outlet check valve is a one-way fluid valve which is oriented to permit free fluid flow from the valve apparatus body 16 into the injection port 55 while preventing fluid flow in the opposite direction. The valve-to-tubing outlet port 13 is connected to the injection port 55 preferably in a direct non-flexible fashion as shown in FIG. 1 or via a short length of tubing or conduit which would then interconnect the valve-to-tubing outlet port 13 to the injection port 55. The interior bore of the valve to tubing outlet port 13 will be made sufficiently small to limit fluid flow out of the valve apparatus 15 to a maximum rate which will be tolerated, in terms of fluid delivery to the needle or catheter 70, by a vein into which the needle or catheter 70 is inserted. The one-way fluid check valves 25 and 50 may be of any suitable type well known to those skilled in the art such as ball, disc, or flap type construction, the only necessity, being that back-flow of fluids through the valves be prevented during operation. All connections to and throughout the valve apparatus 15 are to be sealed and of a permanent nature so as to prevent separation of parts, leakage of fluids, or entrance of air into the system.

The injection port 55 is located between the valve apparatus 15 and downstream tubing 60. The injection port body 56 will generally be constructed of an inflexible material of appropriate thickness to prevent inadvertent extrusion of a hypodermic needles through the body 56. The injection port diaphragm 57 will be a flexible, repeatedly needle pierceable, resealable type generally constructed of natural rubber latex or other synthetic resealable material. The injection port body 56 consists of a hollow conduit 58 fluidly connecting the valve outlet port 13 to the downstream tubing 60. A hollow and fluidly connected leg 59 protrudes out along the length of the hollow conduit 58. The leg 59 will be of an appropriate length or orientation such that the injection port will accept a needle, inserted through the diaphragm 57, up to 1½ inches in length. Further, the leg 59 will be oriented to minimize capture of an air bubble during the priming operation and to facilitate dislodgement of any air bubble that might be thus created. One means of achieving this is by minimizing the length of the leg 59 as shown in FIG. 1. The injection diaphragm 57 is located to sealably cover the end of the leg 59 opposite to that entering the injection port body 56. Further, the diaphragm or injection port may be highly colored in order to facilitate rapid identification by the operator during operation.

Figure 2A:
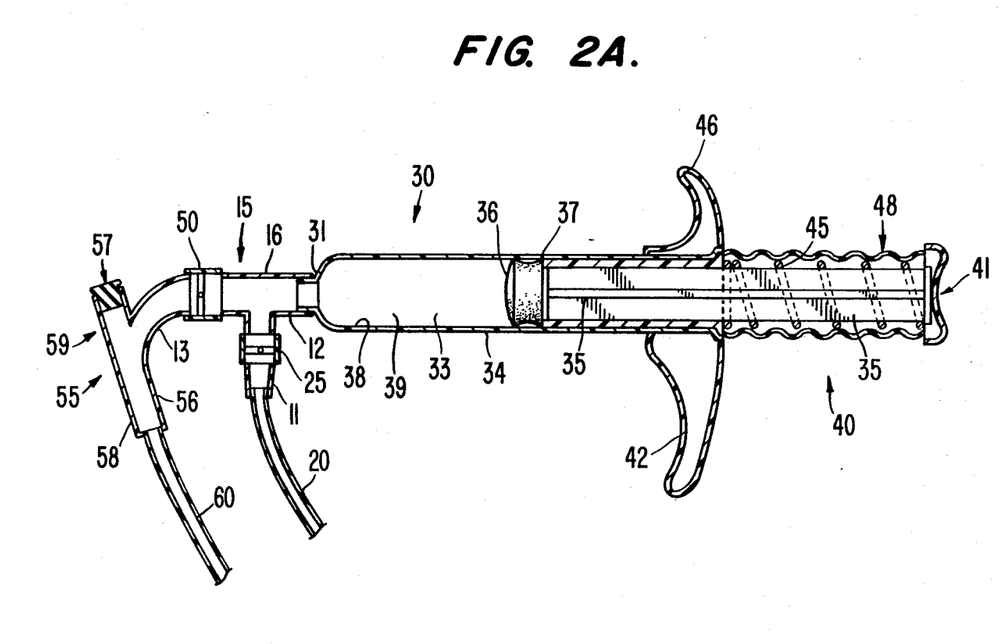
FIGS. 2A, 2B are a cross section elevation of the pump means, syringe recoil mechanism, valve apparatus, and the injection port.
Figure 2B:
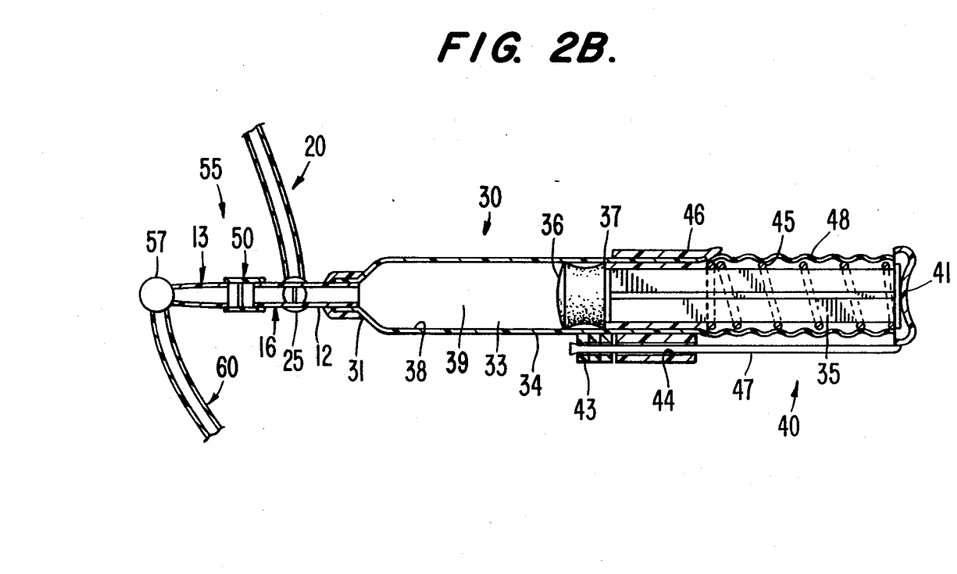

FIG. 2 shows a detailed drawing of the pump means 30 and the automatic recoil mechanism 40. In the present embodiment, the pump means consists of a reusable syringe 33 of the disposable type as is commonly known to those familiar with the art. The syringe consists of a tubular barrel 34 into which a plunger 35 is slidably inserted. The plunger has attached to it, on the end residing inside the barrel, a flexible stopper 36 containing several annular rings 37 serving to fluidly seal the inner bore 38 of the syringe barrel 34 with the stopper 36, thus allowing creation of positive or negative pressure within the syringe chamber 39 by moving the plunger 35. Said stopper 36 has a second purpose of preventing entrance of air into the syringe chamber 39. The syringe size is appropriate to allow delivery of a physiologically adequate flush, for the intended purpose of this invention as described in the opening paragraphs, to be delivered with a minimum of activation of the pump means 30 while maintaining the sterility of the syringe chamber 39. Maintaining sterility of the syringe chamber is achieved by means of restricting the length of travel of the plunger 35 outwardly to less than ½ of the total distance of the barrel 34. This technique of maintaining syringe sterility is well known to those familiar with the art of sterile mixture compounding. As illustrated in FIG. 2, this may be specifically achieved by using a 60 milliliter size syringe 33 with plunger 35 travel restricted by the automatic recoil mechanism 40 to between a zero milliliter and a 25 milliliter graduation on the barrel 34. Sterility will further be maintained by a tube of collapsible material 48, such as natural latex, fit over the exposed section of the plunger 35 and helical spring 45. The tube will be sealably attached to the cap 41 at one end and the attachment means 46 at the other end for the purpose of preventing debris particularly fluids, from contacting the inside of the syringe barrel. In this embodiment, two activations of the invention will present a total of 50 milliliters of flush solution to the valve apparatus 15, injection port 55 downstream tubing 60 and patient FIG. 2 shows the automatic recoil mechanism 40 consisting of an anatomically designed handle 42 continuous with an attachment means 46 to affix the handle to the rear end of the syringe barrel 34 opposite to the nozzle 31. In addition, a guiding rod 47, oriented parallel to the barrel 34 is positioned through an accepting bore 44 in the handle 42 and is permanently attached to a locking ring 43 on the end of the guiding rod 47 oriented towards the nozzle 31 of the syringe 33. The opposite end of the guiding rod 47 is permanently attached to a cap 41 which is itself attached to the end of the plunger 35, opposite to that end to which the stopper 36 is attached. A helical coil spring 45 is located loosely over the plunger 35 and between the attachment means 46 of the handle and the cap 41 such that the spring 45 urges the plunger 35 outwardly from the barrel 34 to the extent that the locking ring 43 on the guiding rod 47 allows.

Figures 7A, 7B:
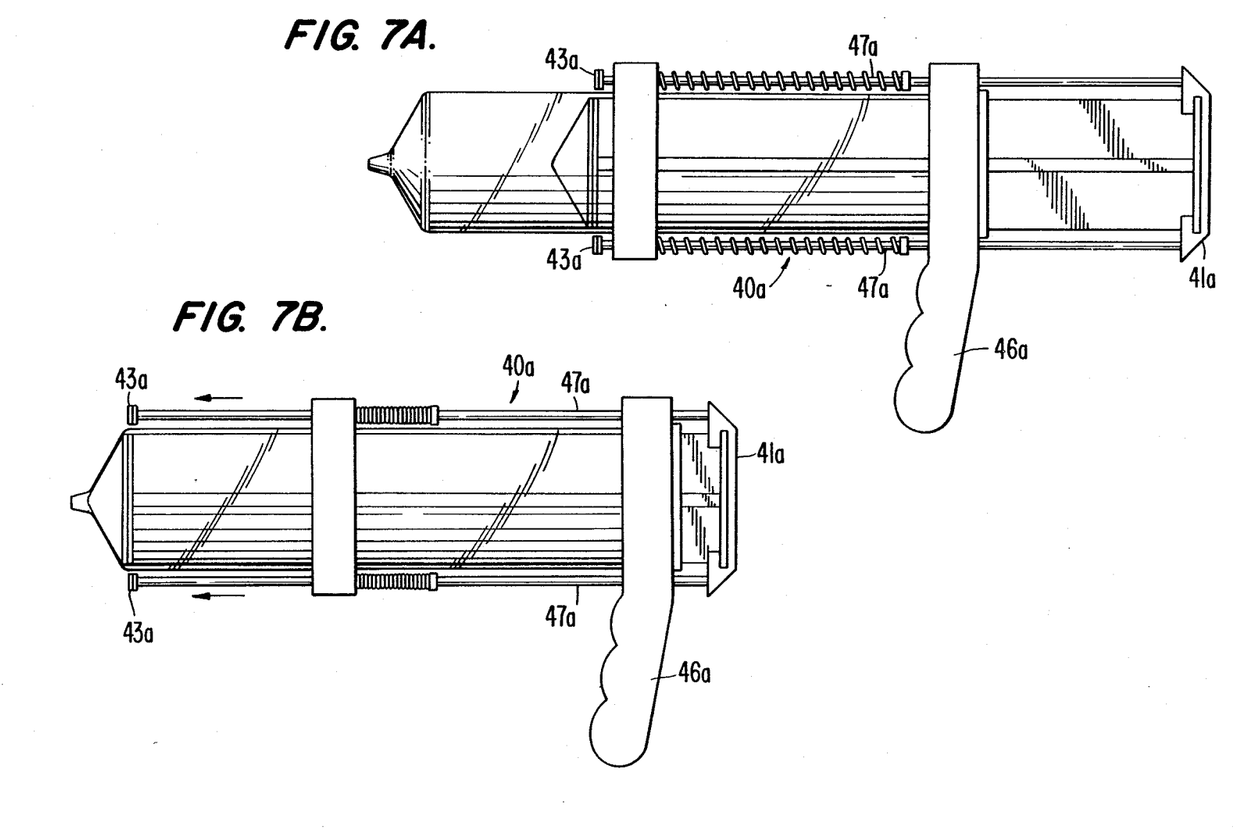
FIG. 7 shows another embodiment of the automatic recoil mechanism with 2 guiding rods.

FIG. 7 shows another embodiment of the automatic recoil mechanism 40a using two guiding rods 47a which are diametrically opposed and located through the attachment means 46a, each having a locking ring 43a, and attached to the cap 41a, for the purpose of providing additional strength and direction during operation of the invention.

The downstream tubing 60 is a length of tubing or conduit interconnecting the injection port 55 to the male luer lock connector 65 at the terminal end of the downstream tubing 60. The downstream tubing 60 is of a minimal length to permit location and operation of the invention at an operationally comfortable distance from the injection site on the patient 66 as shown in FIG. 6.

A Y-site 62 is located at a small distance along the downstream tubing 60 from the male luer lock connector 65. It should be noted that throughout this application a luer lock or luer connector includes both threaded luer locks and tapered male/female luer slip connectors. The Y-site 62 connects to a one way check valve 63 similar to the valves 25 and 50 described in the discussion of the valve apparatus 15 and is oriented to permit fluid flow in the direction towards the downstream tubing 60 while preventing back-flow of fluid away from the downstream tubing 60. The Y-site check valve 63 is connected to an injection port 64 with a standard, needle-pierceable latex diaphragm. As illustrated in FIG. 6 the purpose of the Y-site injection port 64 is to permit introduction of a continuous flow of parenteral fluid 76 for therapeutic purposes or to maintain patency of an intravenous catheter 70 during operation. The Y-site check valve 63 is necessary to prevent back-flow of a critical medication or flush solution up through the Y-site injection port 64 and into the source of parenteral fluid 76.

Slidably movable tubing clamps 67 may be placed at any point along the upstream tubing 20 or downstream tubing 60 for the purpose of closing off the system for any reason.

Translucent plastic protective caps 71 and 72 will be removably attached to the piercing hollow leg 2 on the reservoir spike 5 and to the male luer connector 65 respectively. It is the purpose of these caps to maintain the sterility of these ports during the set-up procedure. It is intended that the caps be removed by the operator immediately prior to connection of these parts to the intended devices during operation (i.e., spike 5 to reservoir container 10 and male luer connector 65 to needle or catheter 70). Further, the entire invention will be sterilized and packaged sterilely in a wrapping which is easily opened during operation and contains instructions for set-up and safe, effective operation.

In operation, the invention is removed from its sterile packaging. The protective cap 71 is removed from the spike 5 and the piercing leg 2 is inserted into a reservoir container 10 which is normally connected to a hanger at a height 2 to 3 feet above the patient. The tubing clamps 67 are left open and the device is primed with reservoir fluid by compressing the plunger fully and releasing it several times in succession to entirely fill all tubings, connectors, the valve apparatus and syringe chamber with reservoir fluid. If a therapeutic parenteral fluid 76 is going to be piggy-backed into the Y-site 62, the fluid should be attached to a standard administration tubing 77 and hypodermic needle 78. The needle should then be aseptically inserted into the Y-site injection port 64 and fluid permitted to flow through the administration tubing 77, hypodermic needle 78, Y-site injection port 64, Y-site check valve 63 and through the terminal end of the downstream tubing 60 such that all air is expelled from these components. (This arrangement is illustrated in FIG. 6). The cap 72 is removed from the male luer connector 65 which is then attached to a needle or catheter 70 which extends into the patients vein.

Figure 3:
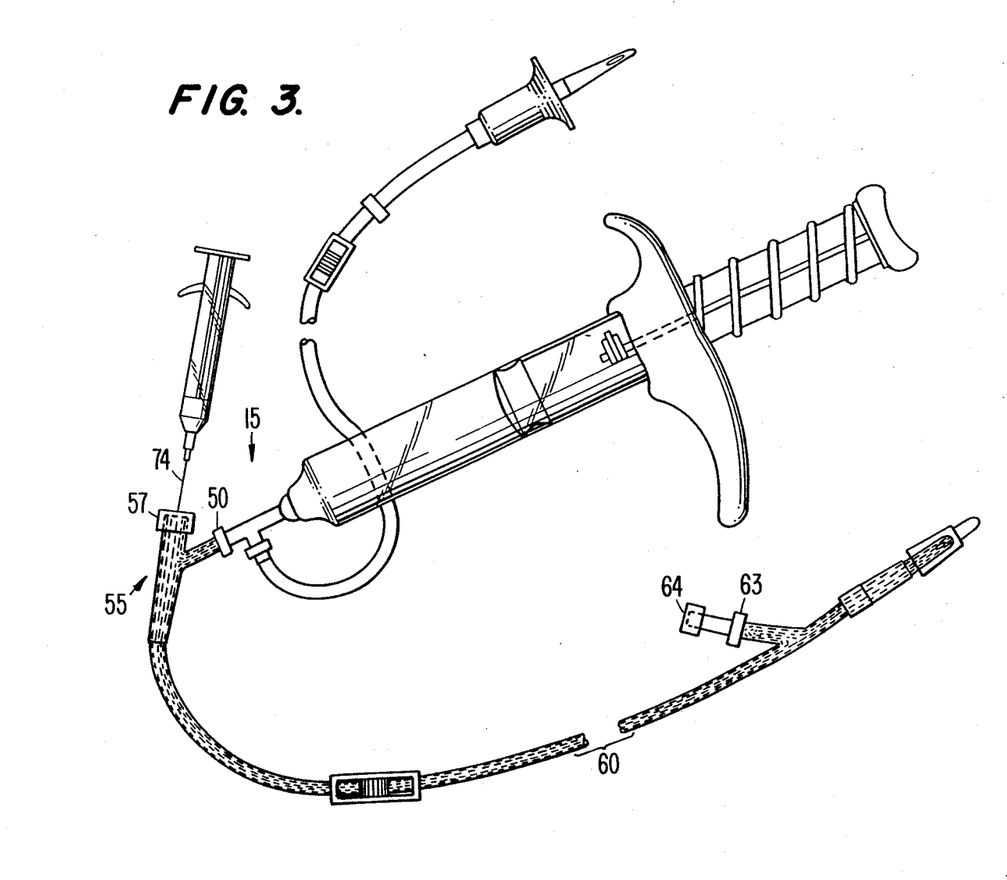
FIG. 3 shows the present invention in particular the valve positions, during injection of a critical medication.

The injection of critical medication is rapidly injected through a hollow needle 74 aseptically inserted into the injection port 55. As illustrated in FIG. 3, as the drug solution is injected, positive pressure created within the downstream tubing 60 closes the outlet check valve 50 and the Y-site check valve 63, preventing back flow of the drug solution into the valve apparatus 15 and the Y-site injection port 64. As the drug solution is injected, reservoir fluid is displaced by the drug solution into the patient. At the end of the injection process, drug solution has been delivered to the downstream tubing 60 and a certain amount (depending upon the volume of the drug solution) into the patient's vein. The hollow needle 74 is then removed from the injection port 55 and the diaphragm 57 reseals itself.

Figure 4:
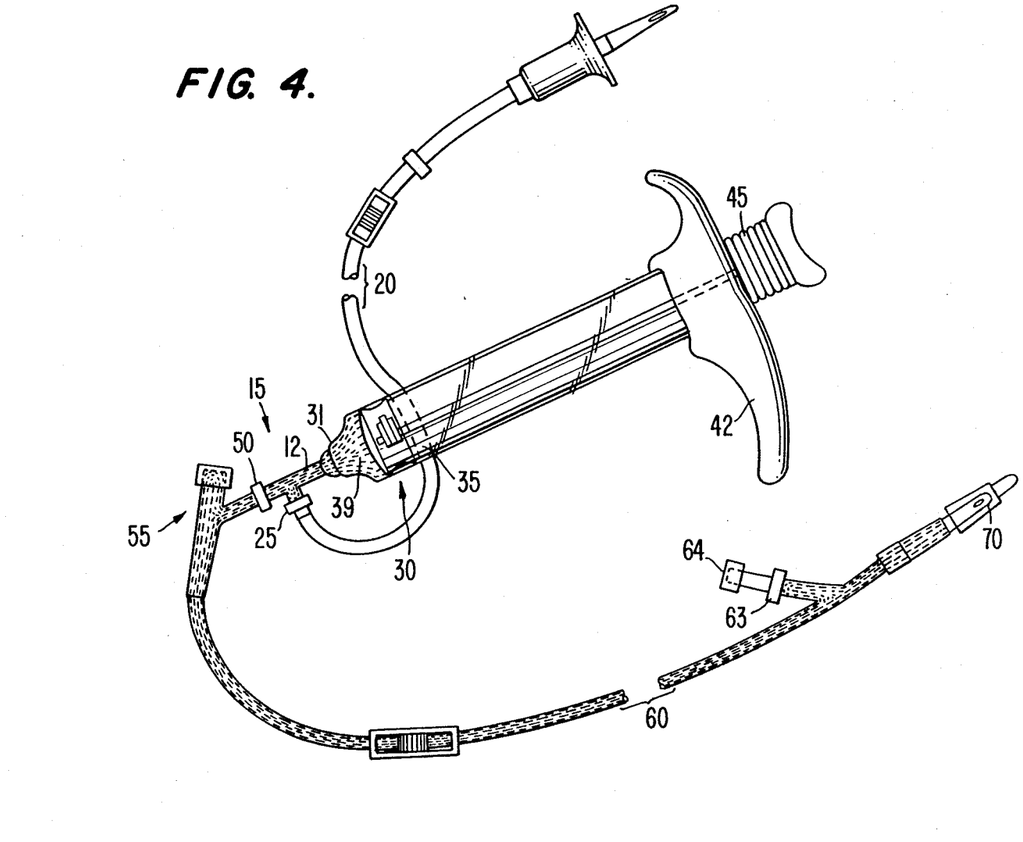
FIG. 4 shows the present invention in particular the valve positions, during the flushing operation.

FIG. 4 shows the flushing phase of operation of the invention which immediately follows the injection of critical medication. The invention handle 42 is firmly gripped by the operator and the plunger 35 is forced rapidly towards the nozzle 31. end of the pump means 30 to the full limit of travel. This operation also compresses the helical spring 45. In doing so, positive pressure is created within the syringe chamber 39 and the reservoir fluid contained within is forced into the valve-to-syringe connector 12, and then into the valve apparatus 15. Within the valve apparatus 15, positive fluid pressure causes the inlet check valve 25 to close, thereby preventing back flow of reservoir fluid into the upstream tubing 20. The pressure further maintains the outlet check valve 50 in an open position allowing reservoir fluid to pass through the valve apparatus 15, injection port 55, and downstream tubing 60. Pressure thus created in the downstream tubing 60 causes the Y-site check valve 63 to close, thereby preventing back flow of medication solution and reservoir fluid into the Y-site injection port 64. As the reservoir fluid passes through the downstream tubing 60, medication solution is forced rapidly through the needle 70 and into the patients venous system.

Figure 5:
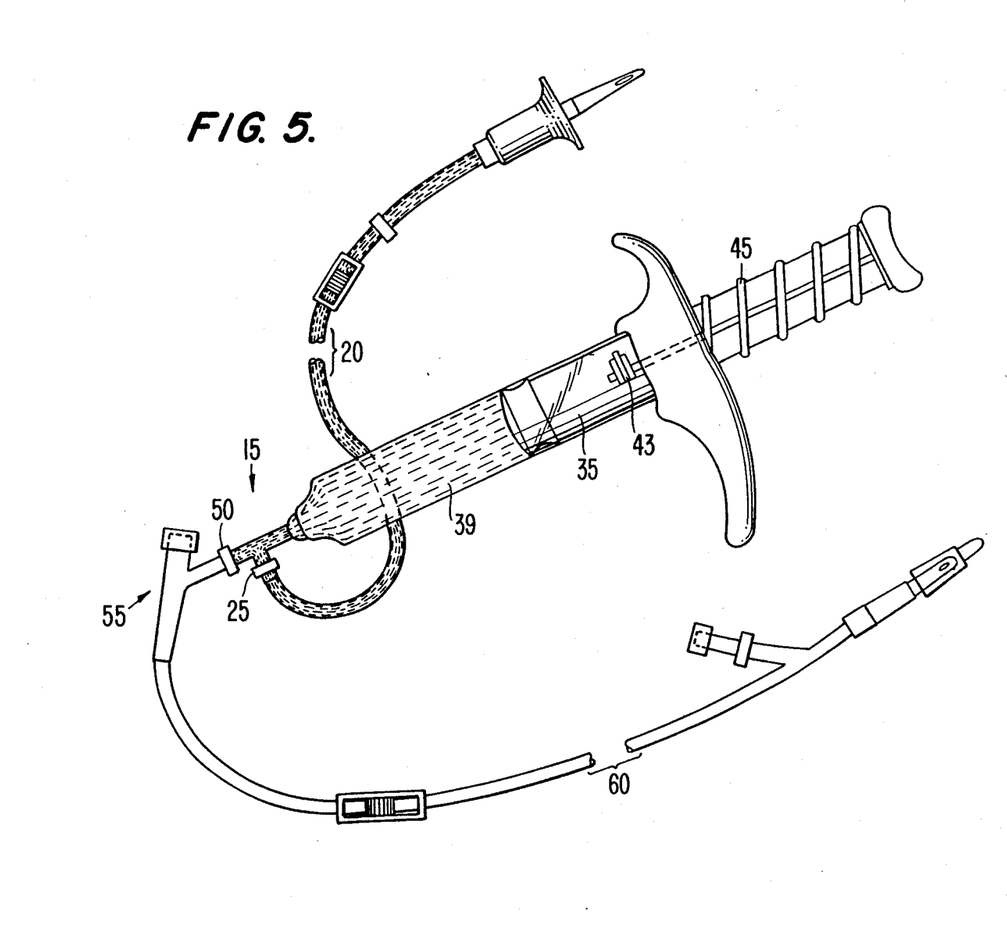
FIG. 5 shows the present invention, in particular the valve positions, during the recoil or refill operation

FIG. 5 illustrates the recoil phase of operation, the function of which is to automatically refill the syringe chamber 39 with a new supply of reservoir fluid for a subsequent flushing operation. In the recoil phase, the previously forced plunger 35 is released by the operator allowing the previously compressed helical spring 45 to force the plunger 35 backwards and thus creating a negative pressure within the syringe chamber 39. The return travel of the plunger 35 is limited by the locking ring 43, thereby resetting the flush volume to the initial amount. The negative pressure thus created opens inlet check valve 25 allowing reservoir fluid to be drawn from the upstream tubing 20 through the valve apparatus 15 and into the syringe chamber 39. At the same time, the negative pressure causes the outlet check valve 50 to close, thereby preventing backflow of any fluid that is contained within the injection port 55, downstream tubing 60, or the patients vein towards or into the syringe chamber 39.

At this point, the invention is refilled and the operator may being the flushing operation again to ensure adequate physiologic flush or the operator may begin the injection operation with another critical medication.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. An apparatus for injecting fluids into a patient comprising:
   (a) means for supplying a flush fluid from a reservoir, said means connected to a first inlet of a valve means, said valve means having at least one outlet and two inlets;
   (b) means, connected to a second inlet of said valve means, for drawing flush fluid through said first inlet and for pumping said flush fluid through at least one outlet of said valve means;
   (c) an injection port having at least two inlets and at least one outlet, a first inlet of said injection port connected to an outlet of said valve means, and a second of said injection port inlets having means for injecting a second fluid into said injection port;
   (d) means for delivering said fluids from said injection port outlet to a patient;
   (e) wherein said means for drawing and pumping flush fluid is a syringe; and
   (f) wherein said syringe further comprises means for automatic recoil.

2. An apparatus for injecting fluids into a patient comprising:
   (i) means for supplying a flush fluid from a reservoir, said means connected to a first inlet of a valve means, said valve means having at least one outlet and two inlets;
   (ii) means, connected to a second inlet of said valve means, for drawing flush fluid through said first inlet and for pumping said flush fluid through at least one outlet of said valve means;
   (iii) an injection port having at least two inlets and at least one outlet, a first inlet of said injection port connected to an outlet of said valve means, and a second of said injection port inlets having means for injecting a second fluid into said injection port;
   (iv) means for delivering said fluids from said injection port outlet to a patient;
   (v) wherein said means for drawing and pumping flush fluid is a syringe having means for automatic recoil; and
   (v) wherein said automatic means for recoil further comprises:
      (a) a handle affixed with an attachment means to a rear end of a syringe barrel opposite a nozzle;
      (b) a plunger inside said tubular barrel, said plunger having a stopper allowing a positive and a negative pressure to be created within said syringe barrel; and (c) a helically coiled spring located loosely over said plunger and between said attachment means and a cap at said rear end of said syringe.

3. An apparatus as recited in claim 2, further comprising means for maintaining sterility by preventing contact with environmental contaminants.

4. An apparatus as recited in claim 3, wherein said means for maintaining sterility comprises a tube of collapsible material fit over an exposed section of said plunger and sealably attached to said cap and attachment means.

5. An apparatus as recited in claim 2, wherein said supply means is a reservoir spike disposed between said valve means and said reservoir.

6. An apparatus as recited in claim 5, further comprising a hydrophilic filter disposed between said reservoir spike and said valve means.

7. An apparatus as recited in claim 2, wherein said second said inlet of said injection port comprises a flexible, repeatedly needle pierceable, resealable diaphragm.

8. An apparatus as recited in claim 7, wherein said diaphragm is formed of natural rubber latex.

9. An apparatus as recited in claim 7, wherein said diaphram is formed of synthetic resealable material.

10. An apparatus as recited in claim 2, wherein said means for delivering fluid from said injection port to a patient comprises a injection means and a luer lock.

11. An apparatus as recited in claim 2, further comprising means for supplying a flow of fluid from a second reservoir into said means for delivering fluids from said injection port outlet to a patient.

12. An apparatus as recited in claim 11, wherein the means for supplying fluids from a second reservoir comprises a check valve means connected between (i) a fluid delivery means connected to said second reservoir and (ii) said delivery means connected to said injection port outlet, said check valve means operating to allow fluid from said second reservoir to flow to a patient when no fluids flow from said injection port outlet and preventing fluid flow from said delivery means connected to said injection port into said delivery means connected to the second reservoir.

13. An apparatus for injecting fluids into a patient as recited in claim 2, wherein, said first inlet has check valve means for preventing flush fluid, flowing in a direction from said first inlet into said valve, from flowing back through said first inlet in an opposite direction;

said outlet having a check valve means for preventing flush fluid, flowing in one direction through said outlet, from flowing back into said valve means in an opposite direction.

14. An method for injecting fluids into a patient comprising:

(a) supplying a flush fluid from a reservoir to a first inlet of a valve means having at least one outlet and 2 inlets;

(b) pumping said flush fluid through at least one outlet of said valve means;

(c) injecting a second fluid into an inlet of an injection port having at least two inlets and at least one outlet, one inlet of said injection port connected to an outlet of said valve means; and (d) delivering said fluids from said injection port outlet to a patient.

15. The method of claim 14 wherein the second fluid comprises a drug.

16. The method of claim 14 wherein the second fluid comprises a diagnostic solution.

17. The method of claim 14 comprising pumping the flush fluid with a syringe.

18. The method of claim 17 comprising maintaining sterility of a chamber of said syringe by restricting a length of travel of a plunger of said syringe to less than one-half of a total distance of a barrel of said syringe, and sealably attaching an exposed section of said plunger of said syringe to a tube of collapsible material.

19. The method of claim 17 further comprising automatically recoiling the syringe.

20. The method of claim 19 wherein the step of automatically recoiling the syringe further comprises:

selecting a locking ring to control an amount of flush;

moving a plunger inside a tubular syringe barrel to create a positive and negative pressure within said syringe barrel; and compressing a helically coiled spring located loosely over said plunger between a means attaching a handle to an end of said syringe barrel opposite a nozzle and a cap at said rear end of said syringe plunger.

21. The method of claim 14 further comprising the steps of:

preventing the flush fluid from flowing back through said first inlet in an opposite direction; and preventing flush fluid flowing in one direction through said outlet from flowing back into said valve means in an opposite direction;

* * * * *